United States Patent [19]

Sariaslani et al.

[11] Patent Number: 5,466,590
[45] Date of Patent: Nov. 14, 1995

[54] CONSTITUTIVE EXPRESSION OF P450SOY AND FERREDOXIN-SOY IN STREPTOMYCES

[75] Inventors: Fateme S. Sariaslani, Newark, Del.; Michael K. Trower, Cambridge, England; Charles A. Omer, Downingtown, Pa.

[73] Assignee: E. I. Du Pont de Nemours and Company, Wilmington, Del.

[21] Appl. No.: 102,863

[22] Filed: Aug. 6, 1993

Related U.S. Application Data

[63] Continuation of Ser. No. 807,001, Dec. 16, 1991, abandoned.
[51] Int. Cl.⁶ .............................. C12P 21/06; C12N 1/20; C12N 15/00; C07H 15/12
[52] U.S. Cl. ................ 435/189; 435/252.35; 435/320.1; 435/69.1; 530/350; 536/23.2; 536/23.4; 536/23.7
[58] Field of Search ............................ 435/69.1, 252.35, 435/320.1, 189; 530/350; 536/23.2, 23.4, 23.7

[56] References Cited

FOREIGN PATENT DOCUMENTS

| WO91/03561 | 3/1991 | European Pat. Off. ........ C12N 15/53 |
| WO93/12236 | 6/1993 | European Pat. Off. ........ C12N 15/53 |

OTHER PUBLICATIONS

J. A. Fornwald et al., "Two promoters, one inducible and one constitutive, control transcription of the *Streptomyces lividans* galactose operon", Proc. Natl. Acad. Sci. USA, vol. 84, pp. 2130–2134 (Apr. 1987).

G. R. Janssen et al., "Tandem promoters, tsrp1 and tsrp2, direct transcription of the thiostrepton resistance gene (tsr) of *Streptomyces azureus*: Transcriptional initiation from tsrp2 occurs after deletion of the −35 region", Mol. Gen. Genet., 221:339–346 (1990).

M. K. Trower et al., "Purification and Characterization of a Soybean Flour–Induced Cytochrome P–450 from *Streptomyces griseus*", Journal of Bacteriology, pp. 1781–1787 (Apr. 1989).

E. Katz et al., "Cloning and Expression of the Tyrosinase Gene from *Streptomyces antibioticus* in *Streptomyces lividans*", Journal of General Microbiology, 129:2703–2714 (1983).

K. Darwish et al., "Engineering proteins, subcloning and hyperexpressing oxidoreductase genes", Protein Engineering, vol. 4, No. 6, pp. 701–708 (1991).

D. P. O'Keefe et al., "Identification of constitutive and herbicide inducible cytochromes P–450 in *Streptomyces griseolus*", Arch. Microbiol., 149:406–412 (1988).

A. M. Thayer, "Bioremediaton: Innovative Technology for Cleaning Up Hazardous Waste", C&EN, pp. 23–44 (Aug. 26, 1991).

D. J. Lydiate et al., "Steptomyces plasmid SCP2:its functional analysis and development into useful cloning vectors", Gene (AMST) 35(3), pp. 223–235.

M. J. Buttner et al., "At Least Three Different RNA Polymerase Holoenzymes Direct Transcription of the Agarase Gene (dagA) of *Streptomyces coelicolor* A3(2)", Cell, vol. 52, pp. 599–607 (Feb. 26, 1988). (Feb. 26, 1988).

C. A. Omer et al., "Genes for Two Herbicide–Inducible Cytochromes P–450 from *Streptomyces griseolus*", Journal of Bacteriology, pp. 3335–3345 (Jun. 1990).

Longo et al, Toxicol. Lett., 44, 289, 1988.

Sariaslani, et al. Biochem. Biophys. Res. Comm., 141, 405, 1986.

(List continued on next page.)

Primary Examiner—Mindy B. Fleisher

[57] ABSTRACT

The present invention provides a method of making a recombinant organism capable of oxidizing organic chemicals by constitutive production of proteins capable of performing oxidation. A recombinant organism and a method of oxidizing organic chemicals are also provided. The present invention is useful in bioremediation to remove waste chemicals from the environment.

7 Claims, 12 Drawing Sheets

OTHER PUBLICATIONS

Horii, et al, *Journal of Bacteriology*, 172(7), 3644–3653, Jul. 1990.

Sariaslani et al, *Development in Industrial Microbiology*, 30, 161–171, 1989.

Trower et al, *Biochemica Et Biophysica Acta*, 1037(3), 290–296, 1990.

Trower et al, *Molecular Microbiology*, 6(15), 2125–2134, 1992.

O'Keefe et al, *Phyto Eff. Envir. Compounds* (Saunders et al, Eds.), Plenum Publishing Corp., 1987, Chap. 6, 151–173.

Trower et al, (*BBRC*), *Biochem. Biophys. Res. Comm.*, 157, 1417–1422, Dec. 30, 1988.

Kallas et al, *Proc. Natl. Acad. Sci.* USA 85, 5794–5798, Aug. 1988.

Suggs et al, *Proc. Natl. Acad. Sci.* USA, 18(11), 6613–6617, Nov. 1981.

Germino et al, *Proc. Natl. Acad. Sci. USA*, 6848–6852, Nov. 1983.

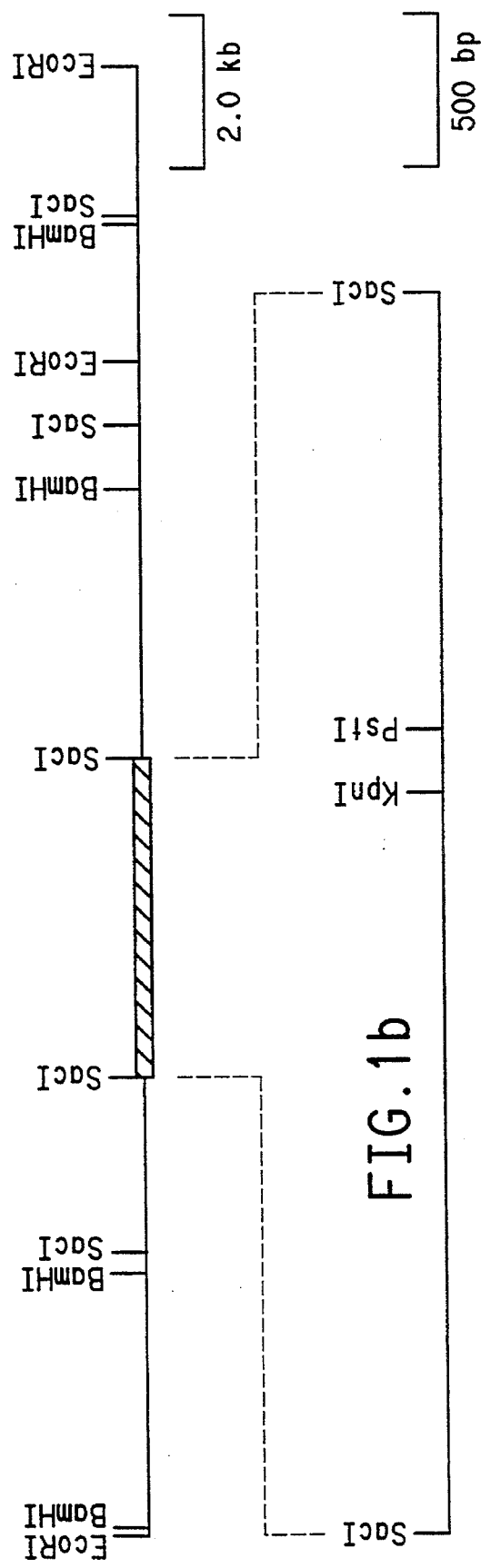
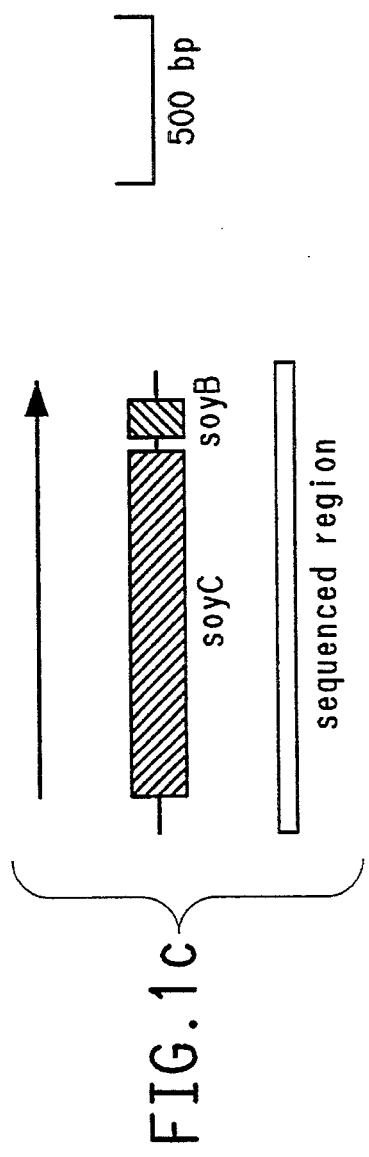
FIG. 1a  FIG. 1b  FIG. 1c

FIG.2a

SEQUENCE DESCRIPTION: SEQ ID NO:10:

```
TACGAACAAC ACCGGCCAGA TCCACGGGCC CGCCGAGCTG GCCGGTCTAC CCGTCGACCA   60
GATAGGTGCC TGAGGCATCT AATAGTGAAG AAGCGCGGAA CGACCGGCTC CGCGGCCACG  120
ACCGAGCACT GCGAGGCGAC CCGATCCCAT GACGGAATCC ACGACGGACC CGGCCCGCCA  180
GAACCTCGAC CCCACCTCCC CGGCCCCCGC GACGTCCTTC CCGCAGGACC GCGGGTGCCC  240
CTACCACCCG CCCGCCGGGT ACGCACCGCT GCGCGAGGGC CGCCCGCTGA GCCGGGTCAC  300
CCTCTTCGAC GGACGCCCGG TCTGGGCGGT CACCGGGCAC GCCCTGGCCC GTCGGCTACT  360
GGCGGACCCG CGGCTCTCCA CCGACCGCAG CCACCCGGAC TTCCCCGTCC CGGCCGAGCG  420
GTTCGCCGGC GCGCAGCGGC GCCGGTCGCG TCCCGACCTT CTCGGTGAAG CCGAGCACAA  480
CACCCAGCGC AGGATGCTCA TCCCGACCTT CTCGGTGAAG CGGATCGGCG CGCTCCGCCC  540
GCGTATCCAG GAGACCGTGG ACCGGCTCCT CGACGCGGAG CGAGCGCATG GAGCGACAAG  600
CGAACTGGTG AGCGCGTTCG CCCTGCCGGT GCCGTCGATG GTGATCTGTG CTCTGCTCGG  660
CGTGCCCTAC GCCGACCACG CGTTCTTCGA GGAACGCTCG CAGCGACTCC TGCGGCGCCC  720
GGGAGCCGAC GATGTGAACA GGGCCCGCGA CGAACTCGAG GAGTACCTGG GCGGCGTGAT  780
CGACCGCAAG AGGGCGGAGC CGGGTGACGG CCTCCTGGAC GAGCTGATCC ACCGGGACCA  840
CCCGGACGGA CCGGTCGACC GCGAACAGCT GGTCGCCTTC GCCGTCATCC TGCTCATCGC  900
```

FIG. 2b

```
CGGGCACGAG ACGACGGCGA ACATGATCTC GCTCGGCACG TTCACGCTGC TGAGCCACCC   960
CGAACAGCTG GCGGGCGCTG GGGCCGGCGG GACGAGCACC GCCGTGGTGG TCGAGGAGCT  1020
GCTGCGGTTC CTCTCCATCG CCGAGGGCCT CCAGCGCCTG GCGACCGAGG ACATGGAGGT  1080
CGACGGGGCG ACGATCCGCA AGGGGGAGGG CGTGGTCTTC TCGACCTCGC TGATCAACCG  1140
CGACGCCGAC GTGTTCCCCC GGGCCCGAGAC ACTCGACTGG GACCGCCCCG CCCGCCATCA  1200
CCTCGCCTTC GGCTTCGGGAG TCCACCAGTG CCTGGGCCAG AACCTGGCCC GCGCCGAGCT  1260
GGACATCGCG ATGGCGCACC TGTTCGAGCG GCTTCCCGGG CTCAGGCTCG CCGTACCCGC  1320
GCACGAGATC CGTCACAAGC CGGGGGACAC GATCCAGGGC CTCCCTCGACC TGCCCGTGGC  1380
CTGGTGAGCG GCGTGGGAGT CCAGGTCGAC AAGGAACGCT GTGTGGGCGC CGGCATGTGT  1440
GCGCTGACCG CGCCGGACGT CGCCGGACTT CTTCACCCCAG GACGACGACG GGTGCTCCCC  1500
GGCCGGGGAGG CGACGTCCGG GACCCATCCG CTGGTGGGGG AGGCGGGTACG GGCCTGCCCG  1560
GTGGGGCGG TGGTCCTCTC CTCCGACTGA CGTCCCCCGG CACGGGGTTC GCCTCTTGCT  1620
GCCATGGCTC GGCGCCGAGG TCAACGACAG CAATCCCAGG GCATTTATGA TGTCTTGATG  1680
CGATCTGTCC CTTGGTGGGC                                              1700
```

FIG.2c

SEQUENCE DESCRIPTION: SEQ ID NO:11:

```
Met Thr Glu Ser Thr Thr Asp Pro Ala Arg Gln Asn Leu Asp Pro Thr
 1               5                  10                  15
Ser Pro Ala Pro Ala Thr Ser Phe Pro Gln Asp Arg Gly Cys Pro Tyr
            20                  25                  30
His Pro Ala Gly Tyr Ala Pro Leu Arg Glu Gly Arg Pro Leu Ser
         35                  40                  45
Arg Val Thr Leu Phe Asp Gly Arg Pro Val Trp Ala Val Thr Gly His
         50                  55                  60
Ala Leu Ala Arg Arg Leu Leu Ala Asp Pro Arg Leu Ser Thr Asp Arg
 65                  70                  75                  80
Ser His Pro Asp Phe Pro Val Pro Ala Glu Arg Phe Ala Gly Ala Gln
            85                  90                  95
Arg Arg Val Ala Leu Leu Gly Val Asp Asp Pro Glu His Asn Thr
        100                 105                 110
Gln Arg Met Leu Ile Pro Thr Phe Ser Val Lys Arg Ile Gly Ala
        115                 120                 125
Leu Arg Pro Arg Ile Gln Glu Thr Val Asp Arg Leu Leu Asp Ala Met
        130                 135                 140
Glu Arg Gln Gly Pro Pro Ala Glu Leu Val Ser Ala Phe Ala Leu Pro
145                 150                 155                 160
```

Val Pro Ser Met Val Ile Cys Ala Leu Leu Gly Val Pro Tyr Ala Asp
165                                170                  175

His Ala Phe Phe Glu Glu Arg Ser Gln Arg Leu Leu Arg Gly Pro Gly
            180                  185                  190

Ala Asp Asp Val Asn Arg Ala Arg Ala Asp Glu Leu Glu Tyr Leu Gly
        195                  200                  205

Ala Leu Ile Asp Arg Lys Arg Ala Glu Pro Gly Asp Gly Leu Leu Asp
210                  215                  220

Glu Leu Ile His Arg Asp His Pro Asp Gly Pro Val Asp Arg Glu Gln
225                  230                  235                  240

Leu Val Ala Phe Ala Val Ile Leu Leu Ile Ala Gly His Glu Thr Thr
            245                  250                  255

Ala Asn Met Ile Ser Leu Gly Thr Phe Thr Leu Leu Ser His Pro Glu
            260                  265                  270

Gln Leu Ala Ala Leu Arg Ala Gly Gly Thr Ser Thr Ala Val Val Val
275                  280                  285

Glu Glu Leu Leu Arg Phe Leu Ser Ile Ala Glu Gly Leu Gln Arg Leu
290                  295                  300

Ala Thr Glu Asp Met Glu Val Asp Gly Ala Thr Ile Arg Lys Gly Glu
305                  310                  315                  320

FIG.2d

```
Gly Val Val Phe Ser Thr Ser Leu Ile Asn Arg Asp Ala Asp Val Phe
                325                 330                 335

Pro Arg Ala Glu Thr Leu Asp Trp Asp Arg Pro Ala Arg His His Leu
                340                 345                 350

Ala Phe Gly Val His Gln Cys Leu Gly Gln Asn Leu Ala Arg
                355                 360                 365

Ala Glu Leu Asp Ile Ala Met Arg Thr Leu Phe Glu Arg Leu Pro Gly
                370                 375                 380

Leu Arg Leu Ala Val Pro Ala His Glu Ile Arg His Lys Pro Gly Asp
                385                 390                 395             400

Thr Ile Gln Gly Leu Leu Asp Leu Pro Val Ala Trp
                405                 410
```

CONSTITUTIVE EXPRESSION OF P450SOY AND FERREDOXIN-SOY IN STREPTOMYCES

This is a continuation of application Ser. No. 07/807,001 filed Dec. 16, 1991, now abandoned.

FIELD OF THE INVENTION

This invention relates to recombinant bacteria of the genus Streptomyces capable of constitutive expression of cytochrome P450soy and the iron-sulfur protein that donates electrons to the cytochrome P450soy. These recombinant bacteria are useful in carrying out a number of important chemical conversions including biotransformation of HMPA and similar compounds.

BACKGROUND OF THE INVENTION

Cytochrome P450 (P450) is a term used for a widely distributed group of unique heme proteins which form carbon monoxide complexes with a major absorption band at wavelengths around 450 nm. These proteins are enzymes which carry out oxidase functions in a wide variety of mixed function oxidase systems involved in biosynthesis and catabolism of specific cell or body components, and in the metabolism of foreign substances entering organisms. Oxygenating enzymes such as P450 appear to be fundamental cellular constituents in most forms of aerobic organisms. The activation of molecular oxygen and incorporation of one of its atoms into organic compounds by these enzymes are reactions of vital importance not only for biosynthesis, but also for metabolic activation or inactivation of foreign agents such as drugs, food preservatives and additives, insecticides, carcinogens and environmental pollutants.

In eukaryotic systems P450, and P450 dependant enzymes are known to act on such xenobiotics and pharmaceuticals as phenobarbitol, antipyrine, haloperidol and prednisone. Known substrates of environmental importance include compounds such as DDT, and a variety of polychlorinated biphenyls and polyaromatic hydrocarbons, as well as other halogenated compounds, including halobenzenes and chloroform.

Hexamethylphosphoramide (HMPA) is a compound that was used heavily by industry in the mid-1970's in the production of aramid fibers and as a general solvent. HMPA is a known carcinogen and has been found to be one of the contaminants at various industrial and chemical waste sites. Studies focusing on the mammalian biodegradation of HMPA are few but it has been found that microsomal P450 isolated from rat liver and nasal mucosa will demethylate HMPA. Longo et al., Toxicol. Lett. 44:289 (1988).

In microbial systems cytochrome P450 is known to oxidize many of the same xenobiotic substrates as in eukaryotic systems and thus can be targeted as possible indicators for the presence of toxic compounds in the environment. One of the earliest reports of xenobiotic transformation was by the bacterium *Streptomyces giseus* which is known to contain the gene for the expression of cytochrome P450. This transformation involved the convention of mannosidostreptomycin to streptomycin. Sariaslani et al., Developments in Industrial Microbiology 30:161 (1989). Since then these reactions have been observed with compounds ranging from simple molecules such as benzene to complex alkaloids (such as vindoline and dihydrovindolin, codein, steroids, and xenobiotics such as phenylhydrazine, ajmaline and colchine. Sariaslani et al., Developments in Industrial Microbiology 30:161 (1989).

Genetically engineered microorganisms with the ability to express the P450 gene offer several potential advantages. Such microorganisms might be designed to express precisely engineered enzymatic pathways that can more efficiently or rapidly degrade specific chemicals. Development efforts are aimed largely at chemicals that are toxic or recalcitrant to naturally occurring bacterial degradation.

It has been shown that bacteria of the genus Streptomyces, when properly induced, are capable of producing both cytochrome P450soy and the iron-sulfur protein (ferredoxin-soy) that donates electrons to cytochrome P450soy. Sariaslani et al., Biochem. Biophys. Res. comm. 141:405 (1986) The induction procedure involves growing the bacteria in a medium comprising an inducer such as soybean flour, genistein or genistin.

The method of Sariaslani et al. for producing P450 is useful however, the need to utilize an inducer such as soybean flour or a soybean flour-like substance to induce production of cytochrome P450soy in bacteria of the genus Streptomyces is a drawback. Such inducers are difficult to work with and represent an unknown variable in the field. Also, the need to induce the bacteria to produce the desired enzyme introduces an additional step in the method, making the method more complex.

There is a need for a simple method of bioremediating methylated phosphoric amides such as HMPA without the use of inducers to stimulate enzymatic activity. A simple method would be based on the use of bacteria capable of constitutive expression of cytochrome P450soy and the iron-sulfur protein that donates electrons to cytochrome P450. The cytochrome P450soy enzyme in *Streptomyces griseus* bears a resemblance in its oxidative reactions to the cytochrome P450 enzymes of mammalian liver microsomes and thus *Streptomyces griseus* could serve as an economical and convenient source of cytochrome P450 for indication of the presence of hazardous chemicals as well as their possible bioremediation.

SUMMARY OF THE INVENTION

One aspect of the present invention provides recombinant bacteria of the genus Streptomyces capable of constitutive expression of cytochrome P450soy and the iron-sulfur protein that donates electrons to cytochrome P450soy.

Another aspect of the present invention provides a process for converting chemicals such as a mutagen or carcinogen into their oxidation products. The process comprises culturing recombinant bacteria of the genus Streptomyces capable of constitutive expression of cytochrome P450soy and the iron-sulfur protein in a culture medium containing the substance to be metabolized.

BRIEF DESCRIPTION OF THE FIGURES

FIG. 1a shows a consensus restriction map generated by BamHI, EcoRI and SacI digestion of a 22 kb region of the *Streptomyces griseus* encoding the P450soy gene. The flanking EcoRI restriction sites are from the vector polylinker.

FIG. 1b shows the restriction map of the heme probe hybridizing 4.8 kb SacI fragment with the endonucleases unique to the M13mp18/19 vector polylinker.

FIG. 1c shows the coding region for soyC and soyB.

FIGS. 2a–2b shows the 1.7 kb nucleotide sequence of *Streptomyces griseus* DNA containing both the soyC and soyB genes.

FIGS. 2c–2e shows the 412 amino acid sequence for the P450-soy protein.

Lane 1= purified P-450$_{soy}$
Lane 2=*Streptomyces griseus* extract grown on YEME medium
Lane 3= *Streptomyces griseus* extract grown on 5×SBG medium
Lane 4=*Streptomyces lividans* C200 extract grown on YEME medium
Lane 5=*Streptomyces lividans* C200 extract grown on 5×SBG medium
Lane 6= *Streptomyces lividans* MM002 (strain 35) extract grown on YEME medium
Lane 7= *Streptomyces lividans* MM002 (strain 35) extract grown on 5×SBG medium
Lane 8= *Streptomyces lividans* MM002 (strain 36) extract grown on YEME medium
Lane 9= *Streptomyces lividans* MM002 (strain 36) extract grown on 5×SBG medium

Figure 3:
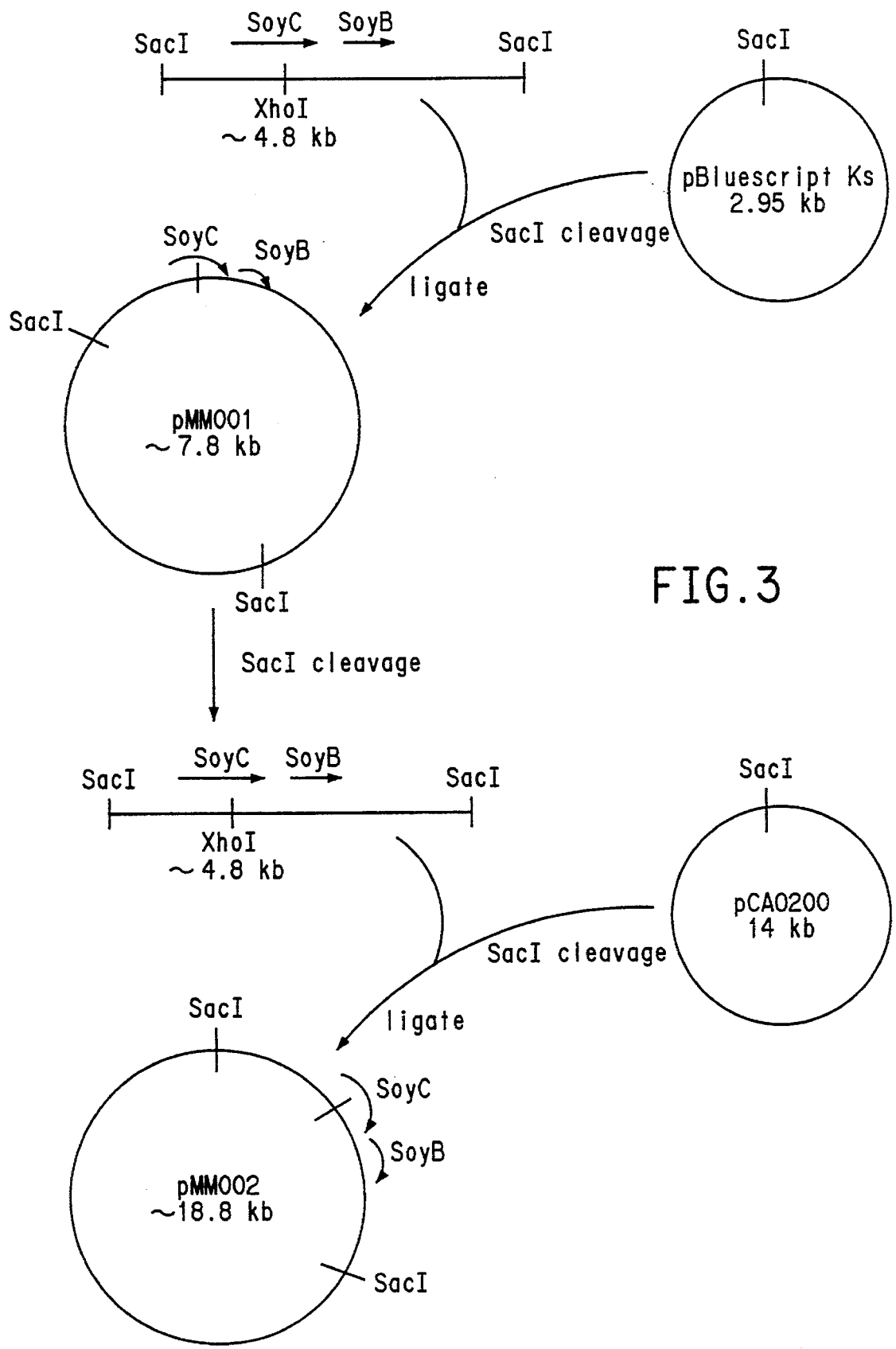
FIG. 3 shows the insertion of the 4.8 kb SacI fragment containing soyC and soyB into pMM001. The subsequent removal of the 4.8 kb fragment from pMM001 and insertion into plasmid pCA0200 to generate pMM002.

Lane 1= purified P-450$_{soy}$
Lane 2=*Streptomyces griseus* extract grown on YEME medium
Lane 3=*Streptomyces griseus* extract grown on 5×SBG medium
Lane 4= *Streptomyces lividans* C200 extract grown on YEME medium
Lane 5= *Streptomyces lividans* C200 extract grown on 5×SBG medium
Lane 6=*Streptomyces lividans* MM007 extract grown on 5× SBG medium
Lane 7= *Streptomyces lividans* MM007 extract grown on YEME medium

DETAILED DESCRIPTION OF THE INVENTION

In the context of this disclosure, a number of terms shall be utilized.

"Promoter" and "promoter region" refer to a sequence of DNA, usually upstream (5') to the protein coding sequence of a structural gene, which controls the expression of the coding region by providing the recognition for RNA polymerase and/or other factors required for transcription to start at the correct site. Promoter sequences are necessary but not always sufficient to drive the expression of the gene.

A "fragment" constitutes a sequence of nucleic acid which can contain an entire gene, less than an entire gene or more than an entire gene.

"Regulation" and "regulate" refer to the modulation of gene expression controlled by DNA sequence elements located primarily, but not exclusively upstream of (5' to) the transcription start of a gene. Regulation may result in an all or non response to a stimulation, or it may result in variations in the level of gene expression.

The term "coding sequence" refers to that portion of a gene encoding a protein, polypeptide, or a portion thereof, and excluding the regulatory sequences which drive the initiation of transcription.

"Construction" or "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

"Transformation" is the acquisition of new genes in a cell after the incorporation of nucleic acid (usually double stranded DNA).

"Operably linked" refers to the chemical fusion of two fragments of DNA in a proper orientation and reading frame to be transcribed into functional RNA.

"Expression" as used herein is intended to mean the transcription and translation to gene product from a gene coding for the sequence of the gene product. In the expression, a DNA chain coding for the sequence of gene product is first transcribed to a complimentary RNA which is often a messenger RNA and, then, the thus transcribed messenger RNA is translated into the abovementioned gene product if the gene product is a protein.

"Translation initiation signal" refers to a unit of three nucleotides (codon) in a nucleic acid that specifies the initiation of protein synthesis.

"Plasmid" as used herein refers to an extra chromosomal element often carrying genes which are not part of the central metabolism of the cell, and usually in the form of circular double-stranded DNA molecules.

"Restriction endonuclease" refers to an enzyme which binds and cuts within a specific nucleotide sequence within double-stranded DNA.

"ATCC" refers to the American Tissue Culture Collection depository located in Rockville, Md. The "ATCC No." is the accession number to cultures on deposit at the ATCC.

"NRRL" refers to the U.S. Department of Agriculture, Northern Regional Research Laboratories, located in Peoria, Ill., and the "NRRL No." is the accession number to cultures on deposit at the NRRL.

The invention involves Streptomyces transformed with two genes from *Streptomyces griseus:* the soyC-encoding cytochrome P450soy and the soyB-encoding ferredoxin-soy that transfers electrons to P450soy. These two genes are transcribed by a constitutive promoter, suaP, from another Streptomyces, *Streptomyces griseolus*. These transformed *Streptomyces lividans* strains constitutively express metabolically active P450soy and thus can metbolize a variety of organic chemicals without having to be induced. The natural promoter for the soyC and the soyB genes, soyP, is not constitutive in *Streptomyces lividans*. This is different from two inducible cytochrome P450 systems (suaC and suaB, and subC and subB) from *Streptomyces griseolus* (ATCC 1176) that metabolize sulfonylureas. The promoters for suaC and suaB, suaP, and the promotors for subC and subB, subP, while requiring induction in *Streptomyces griseolus*, are constitutively expressed when transformed into *Streptomyces lividans* (U.S. patent application Ser. No. 07/464,499 filed Jan. 12, 1990).

The genes encoding cytochrome P450soy (soyC) and ferredoxin-soy (soyB) are contained on a part of a 4.8 kb SacI DNA fragment from *Streptomyces griseus* (ATCC 13273). Alternative sources of this DNA could be *Streptomyces griseus* (ATCC 10137) and *Streptomyces griseus* (ATCC 55185), which also contain proteins similar to, if not identical to cytochrome P450soy of *Streptomyces griseus* (ATCC 13273).

The DNA containing the soyC and soyB genes is operably linked to a promoter sequence, which is capable of constitutively transcribing soyC and soyB in strains of Streptomyces bacteria. The preferred source of this promoter is a 0.6 kb EcoRI-BamHI DNA fragment in pCAO302 from *Streptomyces griseolus* (ATCC 11796). This is the promoter for the suaC and suaB genes which code for cytochrome P450sua and ferredoxin-sua, respectively, in *Streptomyces griseolus* (ATCC 11796). Omer et al., J. Bacteriol. 172:3335(1990). Alternative sources for such a constitutive promoter include but are not limited to one of the promoters for the agarase gene of *Streptomyces coelicolor*, Buttner et al., Cell 52:599(1988), the promoters for the thiostrepton resistance gene from *Streptomyces azureus*, Janssen and Bibb Mol. Gen. Genet. 221:339 (1990), and the constitutive promoter for the *Streptomyces lividans* galactose operon, Fornwald et al., Proc.Natl. Acad. Sci. U.S.A. 84:2130 (1987).

The combination of a constitutive promoter operably linked to the soyC and soyB genes is then introduced into plasmid DNA capable of transforming Streptomyces. The preferred plasmid is pIJ702. Katz et al., J. Gen. Micro. 129:2703(1983). Other plasmids that could be used include but are not limited to derivatives of pIJ101, Kieser et al., Mol. Gen. Genet. 185:223(1982)) and SCP2, Lydiate et al., Gene 35:223 (1985). The plasmid is then cloned into a host Streptomyces strain. The preferred Streptomyces host is *Streptomyces lividans* JI1326. Other Streptomyces host strains that could be used include but are not limited to *Streptomyces griseus* (ATCC 10173), *Streptomyces griseus* (ATCC 13273), *Streptomyces coelicolor* A3 (2) and *Streptomyces parvulus* (ATCC 12434).

Bacterial host strains used include *Streptomyces griseus*, ATCC 13273, *Streptomyces griseolus*, ATCC 11796, and *Streptomyces lividans*, JI1326 (ATCC 53939). The Streptomyces strains were cultured in the following four media: (1) liquid YEME (0.3% yeast extract, 0.5% peptone, 0.3% malt extract, 1.0% glucose, 5 mM $MgCl_2$); (2) 5×SBG (2% glycerol, 0.5% yeast extract, 2.5% soybean flour, 0.5% NaCl, 0.5% $K_2HPO_4$, pH7.0); (3) 1×SBG (2% glycerol, 0.5% yeast extract, 0.5% soybean flour, 0.5% NaCl, 0.5% $K_2HPO_4$, pH7.0); and (4) trypticase soy broth (TSB) (BBL Microbiology Systems, Cockeysville, Md.). Generally, the cultures should be maintained at temperatures between 20°–30° C., preferably between 25°–37° C. with the optimum growth temperature at about 28°–30° C. Cultures were grown by shaking at 28°–30° C. and cells were harvested by centrifugation at approximately 10,000×g for 10–30 min. The pelleted cells were resuspended in DEP buffer (29.3 g/l $Na_2HPO4$-$12H_2O$ or 21.98 g/l $Na_2HPO4$-$7H_2O$, 2.62 g/l $NaH_2PO_4$-$H_2O$, 0.037 g/l $Na_2$ EDTA, 0.154 g/l Dithiothreitol) and sometimes repelleted.

The final pellets were resuspended in DEP buffer and broken in a French pressure cell at 20,000 psi. The broken cells were centrifuged at approximately 40,000×g for 30 minutes and the soluble protein fraction removed and its concentration determined using the BioRad protein assay (Biorad, Richmond, Calif.). Western blots were performed using the procedure described and the antibody to cytochrome P450soy. Trower et al., J. Bacteriol. 171:1781 (1989).

The recombinant bacteria of the present invention are prepared using methods well known to those skilled in the art. For example, transformation of the DNA fragments containing the transcriptional promotor suaP, from the suaC and suaB genes of *Streptomyces griseolus*, upstream of the soyC and soyB genes of *Streptomyces griseus* into *Streptomyces lividans* is performed as described by Hopwood, D. A. et al., Genetic Manipulation of Streptomyces: A Laboratory Manual, The John Innes Foundation, Norwich, UK (1985). Cloning of these DNAs in *E. coli* is performed as described by Maniatis, T. et al., A Guide to Molecular Cloning, Cold Spring Harbor (1982). Restriction enzymes and DNA modification enzymes can be obtained from New England Bioloabs Inc. Beverly, Mass. Taq DNA polymerase can be obtained from Cetus-Perkin Elmer Inc. Following the above procedures, recombinant bacteria *Streptomyces lividans* MM007 was generated from *Streptomyces lividans* JI1326.

The recombinant bacteria of the present invention may be employed to oxidize organic chemicals by culturing recombinant bacteria of the genus Streptomyces capable of constitutive expression of cytochrome P450soy and the iron-sulfur protein that donates electrons to cytochrome P450soy in a culture medium comprising the chemical to be oxidized. The product(s) of oxidation can be determined if required, by standard methods.

It is preferable to use a two stage culturing procedure. In stage one, the bacteria are grown in a suitable culture medium for up to five days at a temperature between about 25° and 37°. In stage two, an aliquot of the stage one culture is transferred to fresh culture medium and maintained for up to five days. The most preferred culturing procedure is carried out by growing the bacteria in stage one at 28°–30° for 3 days, transferring the bacteria to fresh medium and growing in stage two for one additional day at the same temperatures. The second stage culture is then used for the process of the present invention. That is, an aliquot of the substance to be oxidized is incubated with the 24 hr. old second stage cultures.

For example, a first stage culture is prepared by combining 0.5 ml of a spore preparation from *Streptomyces lividans* pMM007 with 25 ml of YEME medium, plus 50 ml of a 2.5M $MgCl_2$ solution and 62.5 µl of a 4 mg/ml stock solution of thiostrepton. This is then incubated at 28°–29° for 72 hours in a gyrotary shaker. The second stage culture is prepared by adding a 2.5 ml portion of the first stage culture to 25 ml of fresh medium. Finally, 5 mg of the substance to be evaluated (e.g., benzo[a]pyrene or benzidine) is dissolved in a solvent such as dimethylsulfoxide (DMSO) and added to the 24 hr. old described second stage culture and incubated for an additional 1 to 10 days. Liquid substrates are added directly to the medium. Samples (5 ml) are periodically taken from these cultures and analyzed by standard methods for the presence of oxidation products.

Recombinant bacteria provided by this invention may be utilized to carry out many commercially important oxidation reactions, as will be recognized by those skilled in the art. The compounds which may be oxidized by the provided recombinant bacteria (and the oxidized compound resulting therefrom) include but are not limited to the following: hexamethylphosphoramide (HMPA), pentamethylphosphoramide (PMPA), tetramethylphosphoramide (TetraMPA), trimethylphosphoramide, (TriMPA), 7-ethoxycoumarin (7-hydroxycoumarin); precocene II (precocene-diol); anisole (phenol, 2-OH anisole); benzene (phenol); biphenyl (4-OH biphenyl); chlorobenzene (2-OH chlorobenzene); coumarin (7-OH coumarin); naphthalene (1-OH naphthalene); transstilbene (4-OH stilbene, 4,4'-di-OH stilbene); toluene (2-OH toluene); glaucine (predicentrine, norglaucine); 10, 11-dimethoxyaporphine (apocodeine, isoapocodeine); papaverine (6-desmethylpapaverine, 7-desmethylpapaverine, 4'-desmethylpapaverine); d-tetrandrine (N'-nortetrandrine); thalicarpine (hernandalinol); bruceantin (side chain alcohols, epoxide); vindoline (dihydrovindoline ether, dihydrovindoline ether dimer, dihydrovindoline ether enamine); dihydrovindoline (11-desmethyldihydrovindoline); leurosine (12'-hydroxy-leurosine); and codeine (14-hydroxycodeine).

EXAMPLES

General Methods

Cloning and DNA sequencing of the soyC and soyB genes encoding cytochrome P450soy and ferredoxin-soy Cytochrome P450soy was purified from *Streptomyces griseus* ATCC 13273 as described. Trower et al., J. Bacteriol. 171:1781 (1989). Two similar forms of cytochrome P450soy were isolated. P450soyΔ, is derived from P450soy by in vitro proteolysis during isolation. Trower et al., J. Bacteriol. 171: 1781 (1989) . Purified P450soy protein was alkylated with 4-vinylpyridine and 5 nanomoles of the alkylated cytochrome P450soy was digested with trypsin as described by Trower et al., J. Bacteriol. 171:1781(1989). The resulting peptide fragments were resolved by reverse phase high performance liquid chromatography as described by Trower et al., J. Bacteriol. 171:1781(1989). One of the tryptic peptide fragments of cytochrome P450soy and one of the P450soyΔ protein were subjected to automated Edman degradation to determine the partial amino acid sequence of the protein/peptide. The $NH_2$-terminal sequence of the P450soyΔ protein is (Seq. No. 1):

Thr Thr Asp Pro Ala Arg Gln Asn Leu Asp Pro Thr Ser Pro Ala Pro.
1            2                  10               15

The $NH_2$ terminal sequence of the tryptic peptide is (Seq. No. 2):

His His Leu Ala Phe Gly Phe Gly Val His Gln Cys Leu Gly Gln Asn.
1              5                   10                  15

A mixture of oligonucleotides that consist of possible DNA sequences that could encode the amino acids FGVHQCL of the tryptic peptide was made. It consists of the following sequence: 5'- TTCGG (G or C)GT(G or C)CACCAGT-GCCT- 3' (Sequence ID NO. 3–6). During synthesis of the oligonucleotide mixture, the two positions indicated as (G or C) consisted of an equal mixture of G or C and thus the oligonucleotide mixture consists of a total of four different species.

A DNA library was constructed in the vector EMBL4 using DNA from *Streptomyces griseus* ATCC 13272 using the procedures described. Omer et al., J. Bacteriol. 172:3335 (1990). The oligonucleotide mixture was [$^{32}$P]-end labeled using T4 polynucleotide kinase, Maniatis, T. et al., A Guide to Molecular Cloning, Cold Spring Harbor,(1982), and used to probe the EMBL4 library of *Streptomyces griseus* DNA as described in Maniatis, T. et al., A Guide to Molecular Cloning, Cold Spring Harbor,(1982), under the following conditions: Prehybridization and hybridization were carried out in 6×SSC (1×SSC is 0.15M NaCl, 0.015M sodium citrate)+ 0.5% SDS at 50° C. Filters were washed twice in 6×SSC+ 0.5% SDS at 50° C. and once in 6×SSC+0.5% SDS at room temperature. Hybridizing plaques were isolated and a 4.8 kb SacI DNA fragment was isolated from one clone that hybridized to the oligonucleotide probe mixture.

A segment of the 4.8 kb SacI DNA fragment was sequenced, Sanger et al., Proc. Natl. Acad. Sci. U.S.A. 74:5463 (1977), [FIG. 1] and found to contain an open reading frame of 1236 base pairs encoding a protein of approximately 45,400 molecular weight. Within this open reading frame was a section that corresponded exactly to the amino acid sequence determined from the cytochrome P450soy tryptic peptide described above. The $NH_2$-terminal sequence of the open reading frame starting with amino acid 4 is the same as the amino acid sequence determined for P450soyΔ (other than a serine to cysteine change at amino acid 30 of the open reading frame). We have named the gene encoding the P450soy protein soyC. Five nucleotides downstream of the stop codon for soyC, another open reading frame of 65 amino acids was identified. This open reading frame shows 40–50% identity to the previously identified ferredoxins of *Streptomyces griseolus*, Ferredoxin-1 and Ferredoxin-2, encoded by the suaB and subB genes respectively. O'Keefe et al., Biochemistry 30:447 (1991). The gene encoding this apparent ferredoxin-like protein from *Streptomyces griseus* is designated soyB and the protein, ferredoxin-soy.

COMPARATIVE EXAMPLE

Figure 5A:
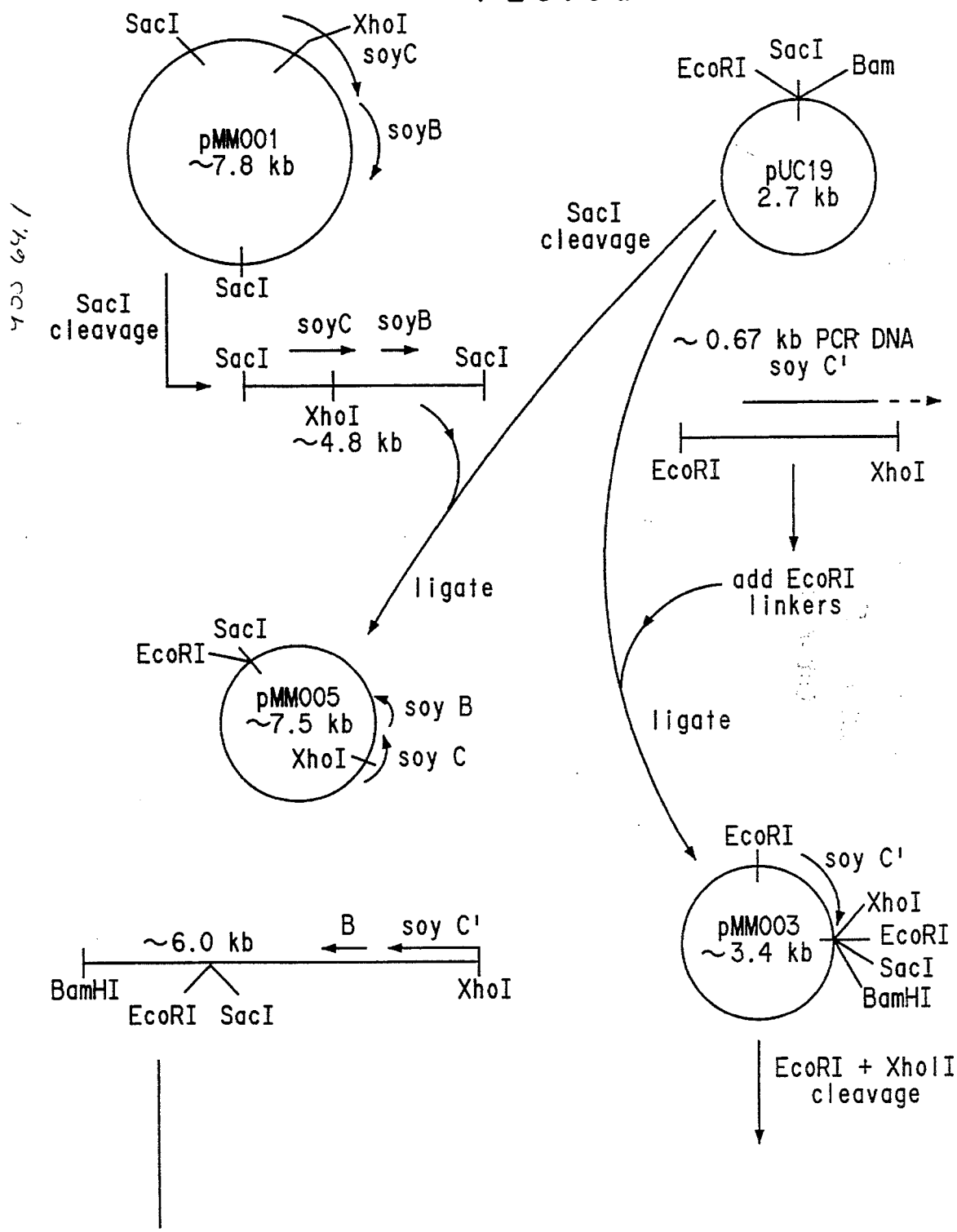
FIGS. 5a–5b shows the generation of pMM004. The insertion of the 4.8 kb SacI fragment containing soyC and soyB into pUC19 at the SacI site to generate pMM005. A DNA fragment containing Streptomyces griseus soyC was amplified so that an EcoRI site was introduced at the 5' end. The new fragment was inserted into pUC19 to generate pMM003. A fragment from pCA0302 containing suaP was ligated to the fragment from pMM003 containing soyC, and a fragment from pMM005 containing soyB and pUC19.
Figure 5B:
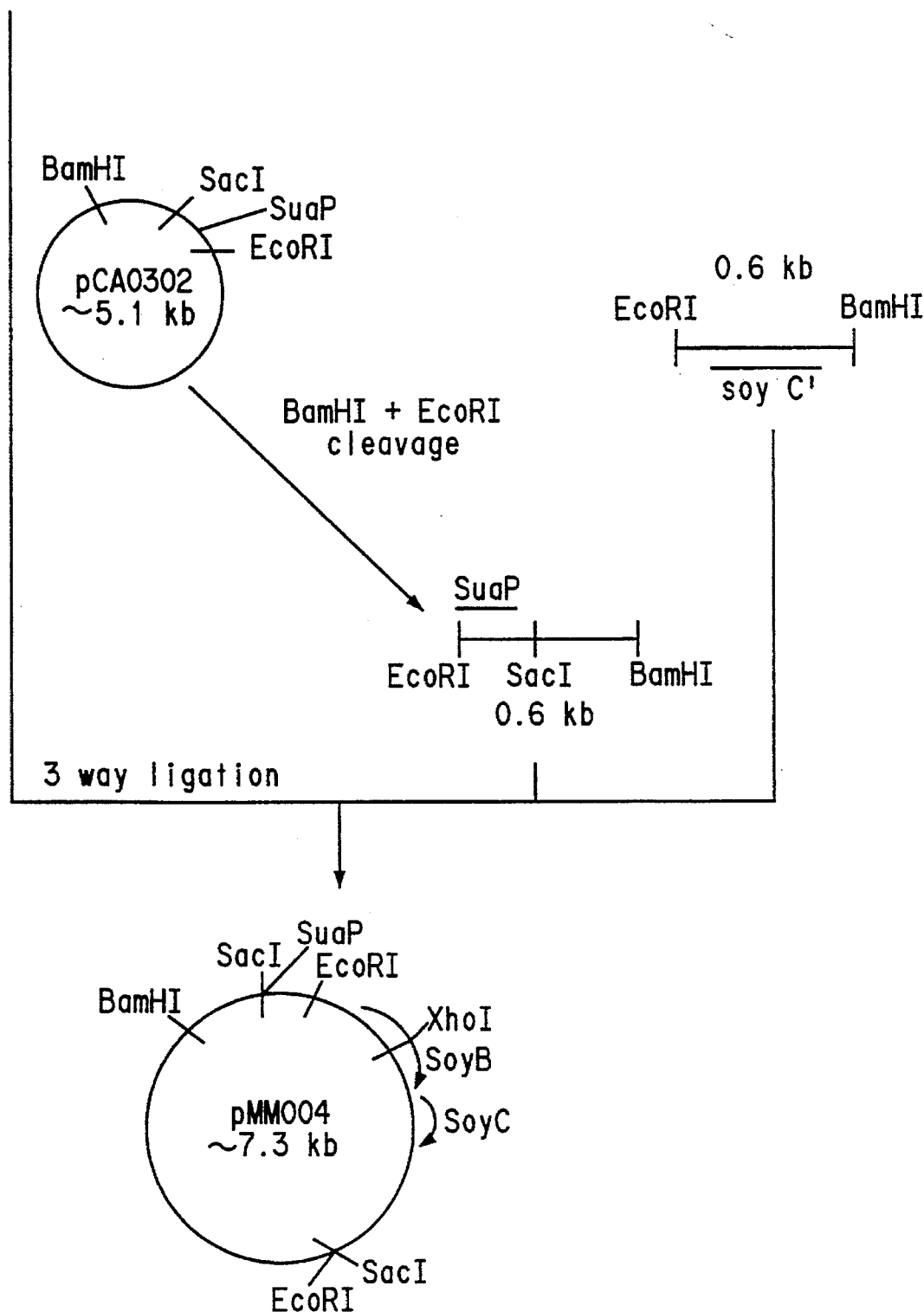

Nonconstitutive Expression of SoyC and SoyB in *Streptomyces lividans* From the SoyP Promoter The 4.8 kb SacI DNA fragment containing the soyC and the soyB genes was cloned (Maniatis et al. 1982) into SacI cleaved pBluescript ks vector (Stratagene Inc., San Diego, Calif.) generating plasmid pMM001 (FIG. 3) and into SacI cleaved pUC19, Yanisch-Peron et al., Gene 33:103(1985), generating plasmid pMM005 (FIG. 5). The 4.8 kb SacI insert was then removed from pMM001 and cloned into the SacI site of pCAO200, Omer et al., J. Bacteriol. 170:2174 (1988) generating pMM002 (FIG. 5). The plasmid pMM002 was transformed into *Streptomyces lividans* generating *Streptomyces lividans* MM002 (FIG. 5).

Two independent strains of *Streptomyces lividans* MM002 and one of *Streptomyces lividans* C200 containing the vector pCAO200 were each grown in 2×25 ml YEME medium containing 8.5% sucrose for approximately 60 hrs at 30° C. One of each of these cultures was subcultured in 100 ml of YEME medium containing 4.25% sucrose and the other in 100 ml of 5×SBG medium. After growth at 30° C. for 48 hrs, an additional 100 ml of growth medium was added and the cells grown for an additional 3 hrs. The cells were harvested and processed as described in the Material and Methods to obtain soluble protein extracts of each of the strains grown in the two different media. A ten microgram sample of each protein was analyzed for the presence of cytochrome P450soy by Western blot analysis.

Figure 4:
FIG. 4 is a Western blot of protein extracts of *Streptomyces griseus, Streptomyces lividans* C200 and *Streptomyces lividans* MM002 from the comparative example described below. It shows that the promotor on SoyB and SoyC is regulated in *Streptomyces lividans*.

In FIG. 4, high levels of P450soy are seen only in the lanes containing purified P450soy protein and in *Streptomyces lividans* MM002 that has been grown in 5× SBG. Much lower levels are seen when *Streptomyces lividans* MM002 was grown in YEME. Thus in *Streptomyces lividans* expression of P450soy from the 4.8 kb SacI *Streptomyces griseus* (ATCC 13272) DNA fragment was induced by soybean flour as it is in *Streptomyces griseus*. This is different from the cytochrome P450 taken from *Streptomyces griseolus*. The genes for the two sulfonylurea inducible cytochromes P450 in *Streptomyces griseolus* when transformed into *Streptomyces lividans* are constitutively expressed and do not require the presence of inducers.

EXAMPLE 1

Recombinant Streptomyces Lividans that constitutively express cytochrome P450

In order to constitutively express cytochrome P450soy in *Streptomyces lividans*, the transcriptional promoter, suaP, from the suaC and suaB genes of *Streptomyces griseolus* was cloned upstream of the soyC and soyB genes. suaP is located upstream of the *Streptomyces griseolus* (ATCC 11796) suaC gene and is located on a 0.6 kb EcoRI-BamHI fragment of pCAO302. Omer et al., J. Bacteriol. 172:3335 (1990). An EcoRI site was introduced 23 bp upstream of the ATG start codon of soyC of *Streptomyces griseus* by performing a polymerase chain reaction. Mullis, K. et al., Cold Spring Harbor Symp. Quant. Biol. 51:263 (1986). A pair of primers were used to carry out PCR on the soyC gene. One oligonucleotide 5'CAGAATTCGCACTGCGAGGCGAC 3' (Sequence ID NO. 8) contained 15 base pairs upstream of the soyC gene along with an EcoRI site near its 5' end. The other oligonucleotide was 5' GATCAGCGCGCCCAGG-TACTCC 3' (SEQUENCE ID NO. 9) and is homologous to a region adjacent to an XhoI site within the soyC gene. When these two oligonucleotides were used to amplify soyC using pMM001 as template an approximately 0.67 kb fragment was amplified. The conditions used for amplification of this DNA were as follows: 10 mM Tris-Cl pH 8.3, 0.05M KCl, 1.5 mM $MgCl_2$, 0.001% gelatin, 0.2 mM each dATP, dTTP, dCTP and 0.05 mM dGTP plus 0.15 mM 7-deaza-dGTP. Each oligonucleotide was used at 1 mM, 10 ng pMM001 template and 2.5 units of Taq polymerase was used in a 100 µl reaction. The temperatures used for amplification were:

1. 100° C., 2 min; 92° C., 5 min (add Taq polymerase); 72° C., 2 min; 1 cycle;
2. 96° C., 1 min; 47° C., 1 min; 72° C., 2 min; 5 cycles;
3. 96° C., 1 min; 65° C., 1 min; 72° C., 2 min; 25 cycles; and
4. 72° C., 5 min; 1 cycle.

The amplified DNA was precipitated with 2M ammonium acetate plus 1 volume isopropanol overnight at −20° C. The precipitate was pelleted at 12,000×g at 4° C. for 15 min, washed twice with 70% ethanol and resuspended in $H_2O$.

The generation of pMM004 occurred as follows. The amplified 0.67 kb fragment of DNA was cloned into the EcoRI site of PUC19, Yanisch-Peron et al., Gene 33: 103 (1985), after adding EcoRI linkers (New England Biolabs, Beverly, Mass.) to the amplified DNA (Maniatis et al. 1982) generating plasmid pMM003. The 4.8 kb SacI fragment containing soyC and soyB was removed from pMM001 and inserted into pUC19 at the SacI site generating plasmid pMM005. A three way ligation was performed between 1) a 0.67 kb EcoRI-XhoI fragment of pMM003 containing one end of soyC with the added EcoRI site, 2) a 0.6 kb EcoRI-BamHI fragment of pCA0302 containing suaP, and 3) an approximately 6.0 kb BamHI-XhoI fragment of pMM005 containing part of the soyC gene, the soyB gene and pUC19. The resulting vector is pMM004 (see FIG. 5).

The generation of plasmid pMM007 occurred as follows. The plasmid pIJ702-322 was made in *E. coli* by ligating SphI cut pIJ702, Katz et al., J. Gen. Microbiol. 129:2703 (1983), to SphI cut pBR322. Hoffman, K. H., et al., J. Basic Microbiol. 30:37 (1990). pIJ702 can replicate in *Streptomyces lividans*, while pBR322 replicates in *E. coli*. pIJ702-322 was cut with SacI and ligated to a 4.1 kb SacI DNA fragment of pMM004 that contains suaP linked to soyC, soyB to generate pMM006. pMM006 was cut with SphI, and self-ligated under dilute conditions (~3 µg/ml) (Maniatis et al. 1982) to separate the pBR322 part of the plasmid from the rest of pMM006 and generating plasmid pMM007 which is capable of replicating in *Streptomyces lividans* but not *E. coli*. This ligated DNA was used to transform *Streptomyces lividans* generating *Streptomyces lividans* MM007 (see FIG. 6).

Transformation of *Streptomyces lividans* was performed as described by Hopwood, D. A. et al., Genetic Manipulation of Streptomyces: A Laboratory Manual, The John Innes Foundation, Norwich, UK (1985). Cloning of DNAs in *E. coli* was performed as described by Maniatis, T. et al., A Guide to Molecular Cloning, Cold Spring Harbor, (1982). Restriction enzymes and DNA modification enzymes were obtained from New England Bioloabs Inc. Beverly, Mass. Taq DNA polymerase were obtained from Cetus-Perkin Elmer Inc.

Figure 7:
FIG. 7 is a Western Blot of protein extracts from *Streptomyces griseus, Streptomyces lividans* C200 and *Streptomyces lividans* MM002 showing that *Streptomyces lividans* MM002 expresses P450soy constitutively.

25 ml cultures of *Streptomyces lividans* transformed with pIJ702 and *Streptomyces lividans* MM007 were grown at 30° C. for 60 hrs. in YEME medium or 5× SBG medium with 5 µg/ml of thiostrepton. *Streptomyces griseus* was grown at 30° C. for 60 hrs. in YENrE medium or 5×SBG medium. After 60 hrs., 10 ml of fresh medium was added to each culture and the cultures were incubated for an additional 2 hrs. 45 min. with shaking at 30° C. The cultures were harvested and soluble protein fractions were isolated from each culture. A Western blot of proteins from the cultures was performed to detect expression of cytochrome P450soy. As can be seen in FIG. 7, expression of cytochrome P450soy in *Streptomyces lividans* MM007 is at least as high as in *Streptomyces griseus* and addition of soybean flour is not required for high level expression of P450soy in *Streptomyces lividans* MM007.

EXAMPLE 2

*Streptomyces lividans* MM007 was grown (25 ml culture) according to the two-stage fermentation protocol. The medium used for cultivation of the organism was YEME containing: yeast extract (3 g/l); peptone (5 g/l); malt extract (3 g/l); glucose (10 g/l); sucrose (340 g/l); $MgCl_2$ from a 2.5M solution (2 ml/L). Thiostrepton was added to insure the maintenance of the plasmid in the organism (62.5 microliter from a stock solution of 4 mg/ml). The first stage cultures were started from spore suspensions of *Streptomyces lividans* MM007. After 3 days of growth on stage one, a 20% inoculum was used to start a stage two culture in fresh YEME medium. After 24 hours, 3 ml of HMPA was added to the culture and at 24 hr and 48 hr 5 ml samples were drawn and extracted with 3 ml of ethyl acetate. The mixture was vigorously extracted by vortexing and allowing the organic and aqueous layers to separate. The organic layer was transferred to a glass vial and evaporated under a stream of nitrogen.

Gas chromatography and mass spectrophotometric (GC/MS) analysis (using a Carbowax capillary column (J. W. Scientific, Folsum, Calif.), 20 m, with a temperature gradient of 60 to 200 at 10° per min) indicate degradation of HMPA by *Streptomyces lividans* MM007. The presence of pentamethyl-phosphoramide (PMPA) and other metabolites were identified. Gas chromatographic analysis was performed on a Varian Vista 6000, Varian Co., Palo Alto, Calif. Mass spectrophotometric analysis was performed on a VG 7070 HS Micromass Mass Spectrometer, Micromass Ltd., Manchester, U.K.

EXAMPLE 3

In another embodiment *Streptomyces lividans* MM007 was used as above with the exception that three, stage one cultures were centrifuged and the resultant cell paste was added to a single 25 ml culture flask containing fresh YEME medium. 0.2 ml of HMPA was immediately added to the second stage culture. Samples were taken as described above. GC/MS analysis demonstrated the presence of many different metabolites. The generation of PMPA and other metabolites by *Streptomyces lividans* MM007 when exposed to HMPA is a strong indication of the ability of *Streptomyces lividans* MM007 to degrade HMPA.

The metabolism of HMPA in Example 3 indicates the utility of *Streptomyces lividans* MM007 for bioremediation of several compounds.

A control experiment was performed in which HMPA was not added to the cultures of *S. lividans* MM007. This culture was extracted as above and analyzed by GC/MS. Apart from one peak seen to be present in all control test samples, none of the peaks observed in HMPA samples and *S. lividans* MM007 were present in control. This data confirms that the peaks observed in test samples were derived from metabolism of HMPA by *S. lividans* MM007.

From the foregoing description, one skilled in the art can easily ascertain the essential characteristics of this invention and, without departing from the spirit and scope thereof, can make various changes and modifications to the invention to adapt it to various usages and conditions.

What is claimed is:

1. A purified nucleic acid fragment comprising a SacI restriction fragment which encodes a cytochrome P-450soy gene which expresses biologically active P-450soy in any Streptomyces species, further comprising a promoter region selected from *Streptomyces griseolus, Streptomyces coelicolor Streptomyces azureus* or *Streptomyces lividans*, the promoter region operably linked to the 5' end of the SacI fragment and further comprising a region coding for ferredoxin soy.

2. A recombinant vector expressible in Streptomyces comprising the nucleic acid fragment of claim 1.

3. A recombinant Streptomyces cell comprising the vector of claim 2.

Figure 6:
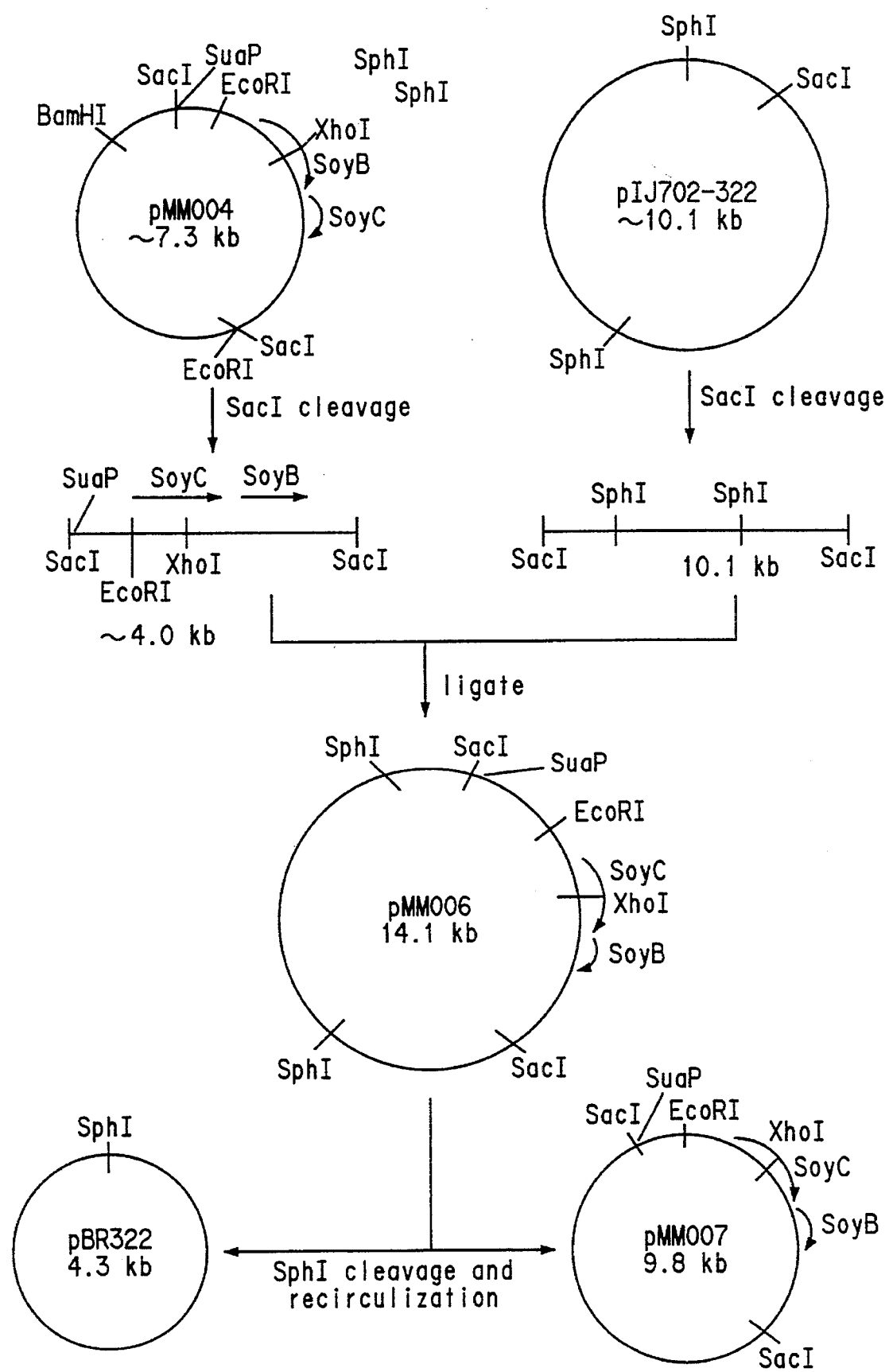
FIG. 6 describes the generation of pMM007 from pMM004 and pIJ702-322. Both pIJ702-322 and pBR322 are cut with SacI and ligated to a 4.1 kb SacI DNA fragment of pMM004 that contains suaP linked to soyC, B to generate pMM005. pMM005 is cut with SphI allowing the separation of the pBR322 and pMM007 plasmids from pMM006.

4. *Streptomyces lividans* containing the vector pMM007 described in FIG. 6.

5. A method of constitutive production of cytochrome P450 soy, comprising:

a) growing the Streptomyces of claim 4 in appropriate medium; and b) isolating cytochrome P450 soy.

6. A DNA molecule consisting of the DNA sequence designated SEQ ID NO.:10.

7. A nucleic acid construct comprising:

a) a first region coding for *Streptomyces griseus* ferredoxin-soy;

b) second region coding for *Streptomyces griseus* cytochrome P-450soy, said second region being upstream of the ferredoxin-soy coding region; and c) a third region coding for a promoter cloned from *Streptomyces griscolus* which constitutively transcribes SoyC and SoyB in Streptomyces bacteria; the third region operably linked to and upstream of the first region.

\* \* \* \* \*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Thr Thr Asp Pro Ala Arg Gln Asn Leu Asp Pro Thr Ser Pro Ala Pro
 1               5                  10                  15
Ala Thr Ser Phe Pro Gln Asp Arg Gly Ser Pro Tyr His Pro
            20                  25                  30
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

```
His His Leu Ala Phe Gly Phe Gly Val His Gln Cys Leu Gly Gln Asn
 1               5                  10                  15
Leu Ala Arg
```

( 2 ) INFORMATION FOR SEQ ID NO:3:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

TTCGGGGTGC ACCAGTGCCT 20

(2) INFORMATION FOR SEQ ID NO:4:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

TTCGGGGTCC ACCAGTGCCT 20

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

TTCGGCGTGC ACCAGTGCCT 20

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

TTCGGCGTCC ACCAGTGCCT 20

(2) INFORMATION FOR SEQ ID NO:7:

(i) SEQUENCE CHARACTERISTICS:
(A) LENGTH: 7 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:7:

Phe Gly Val His Gln Cys Leu
1               5

(2) INFORMATION FOR SEQ ID NO:8:

(i) SEQUENCE CHARACTERISTICS:
(A) LENGTH: 23 base pairs
(B) TYPE: nucleic acid
(C) STRANDEDNESS: single 5,466,590

15 16

-continued (D) TOPOLOGY: linear (i i) MOLECULE TYPE: DNA (genomic)

(x i) SEQUENCE DESCRIPTION: SEQ ID NO:8:

CAGAATTCGC ACTGCGAGGC GAC  23

(2) INFORMATION FOR SEQ ID NO:9:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:9:

GATCAGCGCG CCCAGGTACT CC  22

(2) INFORMATION FOR SEQ ID NO:10:

(i) SEQUENCE CHARACTERISTICS:
(A) LENGTH: 1735 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:10:

| ATATCTTTAC | TACGAACAAC | ACCCCTTGGT | GGGCATACGA | ACAACACCGG | CCAGATCCAC | 60 |
| GGGCCCGCCG | AGCTGGCCGG | TCTACCCGTC | GACCAGATAG | GTGCCTGAGG | CATCTAATAG | 120 |
| TGAAGAAGCG | CGGAACGACC | GGCTCCGCGC | GCACGACCGA | GCACTGCGAG | GCGACCCGAT | 180 |
| CCCATGACGG | AATCCACGAC | GGACCCGGCC | CGCCAGAACC | TCGACCCCAC | CTCCCCGGCC | 240 |
| CCCGCGACGT | CCTTCCCGCA | GGACCGCGGG | TGCCCCTACC | ACCCGCCCGC | CGGGTACGCA | 300 |
| CCGCTGCGCG | AGGGCCGCCC | GCTGAGCCGG | GTCACCCTCT | TCGACGGACG | CCCGGTCTGG | 360 |
| GCGGTCACCG | GCACGCCCT | GGCCCGTCGG | CTACTGGCGG | ACCCGCGGCT | CTCCACCGAC | 420 |
| CGCAGCCACC | CGGACTTCCC | CGTCCCGGCC | GAGCGGTTCG | CCGGCGCGCA | GCGGCGCCGC | 480 |
| GTCGCTCTGC | TCGGCGTCGA | CGACCCCGAG | CACAACACCC | AGCGCAGGAT | GCTCATCCCG | 540 |
| ACCTTCTCGG | TGAAGCGGAT | CGGCGCGCTC | CGCCCGCGTA | TCCAGGAGAC | CGTGGACCGG | 600 |
| CTCCTCGACG | CGATGGAGCG | ACAAGGGCCC | CCGGCCGAAC | TGGTGAGCGC | GTTCGCCCTG | 660 |
| CCGGTGCCGT | CGATGGTGAT | CTGTGCTCTG | CTCGGCGTGC | CCTACGCCGA | CCACGCGTTC | 720 |
| TTCGAGGAAC | GCTCGCAGCG | ACTCCTGCGC | GGCCCGGGAG | CCGACGATGT | GAACAGGGCC | 780 |
| CGCGACGAAC | TCGAGGAGTA | CCTGGGCGCG | CTGATCGACC | GCAAGAGGGC | GGAGCCGGGT | 840 |
| GACGGCCTCC | TGGACGAGCT | GATCCACCGG | GACCACCCGG | ACGGACCGGT | CGACCGCGAA | 900 |
| CAGCTGGTCG | CCTTCGCCGT | CATCCTGCTC | ATCGCCGGGC | ACGAGACGAC | GGCGAACATG | 960 |
| ATCTCGCTCG | GCACGTTCAC | GCTGCTGAGC | CACCCCGAAC | AGCTGGCGGC | GCTGCGGGCC | 1020 |
| GGCGGGACGA | GCACCGCCGT | GGTGGTCGAG | GAGCTGCTGC | GGTTCCTCTC | CATCGCCGAG | 1080 |
| GGCCTCCAGC | GCCTGGCGAC | CGAGGACATG | GAGGTCGACG | GGCGACGAT | CCGCAAGGGG | 1140 |
| GAGGGCGTGG | TCTTCTCGAC | CTCGCTGATC | AACCGCGACG | CCGACGTGTT | CCCCCGGGCC | 1200 |
| GAGACACTCG | ACTGGGACCG | CCCCGCCCGC | CATCACCTCG | CCTTCGGCTT | CGGAGTCCAC | 1260 |
| CAGTGCCTGG | GCCAGAACCT | GGCCCGCGCC | GAGCTGGACA | TCGCGATGCG | CACCCTGTTC | 1320 |

```
GAGCGGCTTC  CCGGGCTCAG  GCTCGCCGTA  CCCGCGCACG  AGATCCGTCA  CAAGCCGGGG   1380

GACACGATCC  AGGGCCTCCT  CGACCTGCCC  GTGGCCTGGT  GAGCGGCGTG  GGAGTCCAGG   1440

TCGACAAGGA  ACGCTGTGTG  GGCGCCGGCA  TGTGTGCGCT  GACCGCGCCG  GACGTCTTCA   1500

CCCAGGACGA  CGACGGTCTC  AGCGAGGTGC  TCCCCGGCCG  GGAGGCGACG  TCCGGGACCC   1560

ATCCGCTGGT  GGGGGAGGCG  GTACGGGCCT  GCCCGGTGGG  GGCGGTGGTC  CTCTCCTCCG   1620

ACTGACGTCC  CCCGGCACGG  GGTTCGCCTC  TTGCTGCCAT  GGCTCGGCGC  CGAGGTCAAC   1680

GACAGCAATC  CCAGGGCATT  TATGATGTCT  TGATGCGATC  TGTCCCTTGG  TGGGC        1735
```

( 2 ) INFORMATION FOR SEQ ID NO:11:

( i ) SEQUENCE CHARACTERISTICS:
        ( A ) LENGTH: 412 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:11:

```
Met  Thr  Glu  Ser  Thr  Thr  Asp  Pro  Ala  Arg  Gln  Asn  Leu  Asp  Pro  Thr
 1              5                        10                       15

Ser  Pro  Ala  Pro  Ala  Thr  Ser  Phe  Pro  Gln  Asp  Arg  Gly  Cys  Pro  Tyr
               20                        25                       30

His  Pro  Pro  Ala  Gly  Tyr  Ala  Pro  Leu  Arg  Glu  Gly  Arg  Pro  Leu  Ser
               35                        40                       45

Arg  Val  Thr  Leu  Phe  Asp  Gly  Arg  Pro  Val  Trp  Ala  Val  Thr  Gly  His
     50                        55                       60

Ala  Leu  Ala  Arg  Arg  Leu  Leu  Ala  Asp  Pro  Arg  Leu  Ser  Thr  Asp  Arg
 65                       70                       75                       80

Ser  His  Pro  Asp  Phe  Pro  Val  Pro  Ala  Glu  Arg  Phe  Ala  Gly  Ala  Gln
               85                        90                       95

Arg  Arg  Arg  Val  Ala  Leu  Leu  Gly  Val  Asp  Asp  Pro  Glu  His  Asn  Thr
              100                       105                      110

Gln  Arg  Arg  Met  Leu  Ile  Pro  Thr  Phe  Ser  Val  Lys  Arg  Ile  Gly  Ala
              115                       120                      125

Leu  Arg  Pro  Arg  Ile  Gln  Glu  Thr  Val  Asp  Arg  Leu  Leu  Asp  Ala  Met
     130                       135                      140

Glu  Arg  Gln  Gly  Pro  Pro  Ala  Glu  Leu  Val  Ser  Ala  Phe  Ala  Leu  Pro
145                       150                      155                      160

Val  Pro  Ser  Met  Val  Ile  Cys  Ala  Leu  Leu  Gly  Val  Pro  Tyr  Ala  Asp
               165                       170                      175

His  Ala  Phe  Phe  Glu  Glu  Arg  Ser  Gln  Arg  Leu  Leu  Arg  Gly  Pro  Gly
               180                       185                      190

Ala  Asp  Asp  Val  Asn  Arg  Ala  Arg  Asp  Glu  Leu  Glu  Glu  Tyr  Leu  Gly
               195                       200                      205

Ala  Leu  Ile  Asp  Arg  Lys  Arg  Ala  Glu  Pro  Gly  Asp  Gly  Leu  Leu  Asp
     210                       215                      220

Glu  Leu  Ile  His  Arg  Asp  His  Pro  Asp  Gly  Pro  Val  Asp  Arg  Glu  Gln
225                       230                      235                      240

Leu  Val  Ala  Phe  Ala  Val  Ile  Leu  Leu  Ile  Ala  Gly  His  Glu  Thr  Thr
               245                       250                      255

Ala  Asn  Met  Ile  Ser  Leu  Gly  Thr  Phe  Thr  Leu  Leu  Ser  His  Pro  Glu
               260                       265                      270
```

-continued

| Gln | Leu | Ala 275 | Ala | Leu | Arg | Ala | Gly 280 | Gly | Thr | Ser | Thr | Ala 285 | Val | Val | Val |
| Glu | Glu 290 | Leu | Leu | Arg | Phe | Leu 295 | Ser | Ile | Ala | Glu | Gly 300 | Leu | Gln | Arg | Leu |
| Ala 305 | Thr | Glu | Asp | Met | Glu 310 | Val | Asp | Gly | Ala | Thr 315 | Ile | Arg | Lys | Gly | Glu 320 |
| Gly | Val | Val | Phe | Ser 325 | Thr | Ser | Leu | Ile | Asn 330 | Arg | Asp | Ala | Asp | Val 335 | Phe |
| Pro | Arg | Ala | Glu 340 | Thr | Leu | Asp | Trp | Asp 345 | Arg | Pro | Ala | Arg | His 350 | His | Leu |
| Ala | Phe | Gly 355 | Phe | Gly | Val | His | Gln 360 | Cys | Leu | Gly | Gln | Asn 365 | Leu | Ala | Arg |
| Ala | Glu 370 | Leu | Asp | Ile | Ala | Met 375 | Arg | Thr | Leu | Phe | Glu 380 | Arg | Leu | Pro | Gly |
| Leu 385 | Arg | Leu | Ala | Val | Pro 390 | Ala | His | Glu | Ile | Arg 395 | His | Lys | Pro | Gly | Asp 400 |
| Thr | Ile | Gln | Gly | Leu 405 | Leu | Asp | Leu | Pro | Val 410 | Ala | Trp | | | | |

( 2 ) INFORMATION FOR SEQ ID NO:12:

( i ) SEQUENCE CHARACTERISTICS:
        ( A ) LENGTH: 65 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:12:

| Met 1 | Gly | Val | Gln | Val 5 | Asp | Lys | Glu | Arg | Cys 10 | Val | Gly | Ala | Gly | Met 15 | Cys |
| Ala | Leu | Thr | Ala 20 | Pro | Asp | Val | Phe | Thr 25 | Gln | Asp | Asp | Gly 30 | Leu | Ser | |
| Glu | Val | Leu 35 | Pro | Gly | Arg | Glu | Ala 40 | Thr | Ser | Gly | Thr | His 45 | Pro | Leu | Val |
| Gly | Glu 50 | Ala | Val | Arg | Ala | Cys 55 | Pro | Val | Gly | Ala | Val 60 | Val | Leu | Ser | Ser |
| Asp 65 | | | | | | | | | | | | | | | |